(12) United States Patent
Fishman

(10) Patent No.: US 9,358,027 B2
(45) Date of Patent: Jun. 7, 2016

(54) THORACOSCOPIC INSTRUMENT

(75) Inventor: Daniel Fishman, Houston, TX (US)

(73) Assignee: WEXLER SURGICAL, INC., Houston, TX (US)

( * ) Notice: Subject to any disclaimer, the term of this patent is extended or adjusted under 35 U.S.C. 154(b) by 853 days.

(21) Appl. No.: 13/591,317

(22) Filed: Aug. 22, 2012

(65) Prior Publication Data

US 2014/0058401 A1 Feb. 27, 2014

(51) Int. Cl.
*A61B 17/28* (2006.01)
*A61B 17/29* (2006.01)
*A61B 17/16* (2006.01)
*A61B 17/062* (2006.01)

(52) U.S. Cl.
CPC .......... *A61B 17/2909* (2013.01); *A61B 17/062* (2013.01); *A61B 17/1608* (2013.01); *A61B 17/2833* (2013.01); *A61B 2017/2837* (2013.01); *A61B 2017/2946* (2013.01); *A61B 2017/2947* (2013.01)

(58) Field of Classification Search
CPC ..... A61B 17/00; A61B 17/06; A61B 17/3209
USPC .............. 606/1, 108, 148, 157, 167, 174, 205
See application file for complete search history.

(56) References Cited

U.S. PATENT DOCUMENTS

| | | | |
|---|---|---|---|
| 5,219,354 A * | 6/1993 | Choudhury et al. | .......... 606/174 |
| D365,878 S | 1/1996 | Blake | |
| D366,699 S | 1/1996 | Blake | |
| D366,700 S | 1/1996 | Blake | |
| 5,961,532 A | 10/1999 | Finley et al. | |
| 6,626,929 B1 | 9/2003 | Bannerman | |
| 6,699,254 B1 | 3/2004 | Tontarra | |
| 6,752,821 B2 | 6/2004 | Scholer et al. | |
| 6,802,852 B2 | 10/2004 | Tontarra | |
| 7,052,505 B2 | 5/2006 | Widmann | |
| 7,211,099 B2 | 5/2007 | Lang et al | |
| 7,377,933 B2 | 5/2008 | Martin | |
| 7,662,167 B2 | 2/2010 | Lang et al. | |
| 7,922,718 B2 | 4/2011 | Moses et al. | |
| 8,048,106 B2 | 11/2011 | Widmann | |
| 8,123,743 B2 | 2/2012 | Arts et al. | |

(Continued)

FOREIGN PATENT DOCUMENTS

| DE | 102006043971 A1 | 4/2008 |
|---|---|---|
| EP | 2213254 A1 | 4/2010 |

OTHER PUBLICATIONS

"Modular Laparoscopic Instrumentation" www.marinamedical.com, http://www.marinamedical.com/PDF/Laparoscopic_English.pdf (accessed Jun. 27, 2012).

(Continued)

*Primary Examiner* — Vy Bui
(74) *Attorney, Agent, or Firm* — Kramer & Amado P.C.

(57) ABSTRACT

Various embodiments relate to a surgical instrument. The surgical instrument includes a first handle member having a first handle portion and a first shaft portion; a first end member connected to the first handle member having a first instrument portion and a tab; a second end member connected to the tab of the first end member having a second instrument portion and a shaft portion; a second handle member connected to the shaft portion of the second end member; and a lock that releasably connects the second handle member to the shaft portion of the first handle member.

20 Claims, 8 Drawing Sheets

(56) References Cited

U.S. PATENT DOCUMENTS

| | | |
|---|---|---|
| 2005/0119693 A1 | 6/2005 | Prestel |
| 2007/0112376 A1 | 5/2007 | Propp |
| 2008/0172085 A1 | 7/2008 | Chiu et al. |
| 2010/0222800 A1 | 9/2010 | Rebstock et al. |
| 2012/0143241 A1 | 6/2012 | Ray |

OTHER PUBLICATIONS

"Laparoscopic instruments" http://www.surgical-instruments-usa.info/images/content/en/doc465__rev__f-laparoscopic__catalog.pdf (accessed Jun. 27, 2012).

* cited by examiner

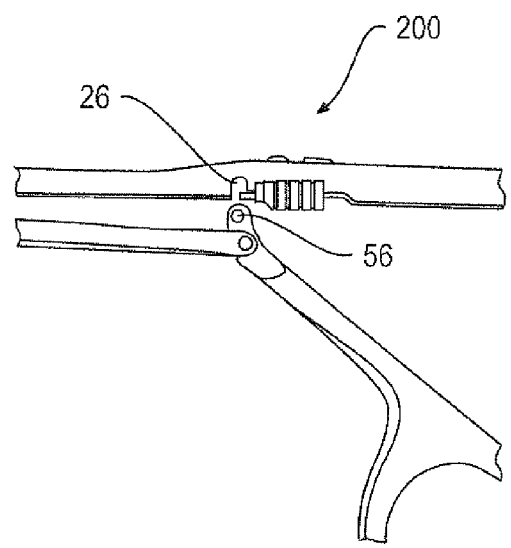
FIG. 6A
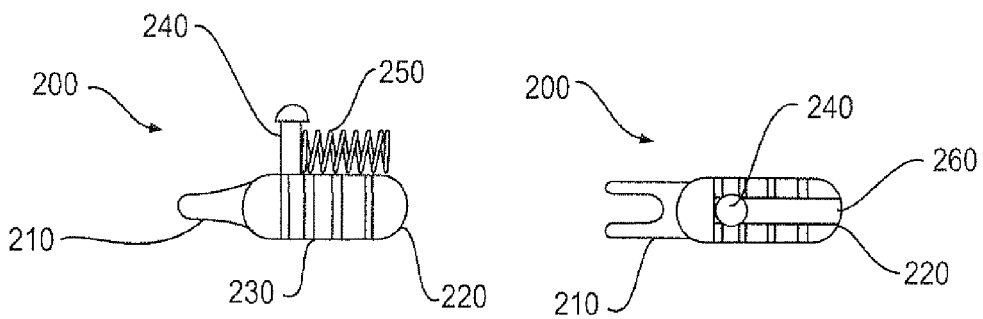
FIG. 6B  FIG. 6C

THORACOSCOPIC INSTRUMENT

BACKGROUND OF THE INVENTION

1. Field of the Invention

This invention relates generally to surgical instruments.

2. Description of Related Art

Surgical instruments used in minimally invasive surgery often include a narrow shaft portion that passes through a small incision or port such as a trocar. In instruments with movable ends, the narrow shaft portion includes moving parts that translate motion from the handle to the movable end. Such instruments can sometimes be difficult to clean because of the close arrangement of moving parts in the shaft portion.

SUMMARY OF THE INVENTION

In light of the present need for a surgical instrument that is easy to clean, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments relate to a surgical instrument. The surgical instrument includes a first handle member having a first handle portion and a first shaft portion; a first end member connected to the first handle member having a first instrument portion and a tab; a second end member connected to the tab of the first end member having a second instrument portion and a shaft portion; a second handle member connected to the shaft portion of the second end member; and a lock that releasably connects the second handle member to the shaft portion of the first handle member.

In various embodiments, the first handle portion has a first ratchet surface extending from an end of the handle portion and the second handle portion has a second ratchet surface extending from an end of the second handle portion.

In various embodiments, the shaft portion of the first handle member includes a slot and the lock releasably retains a pin of the second handle member within the slot.

In various embodiments, wherein the lock includes a threaded shaft having grasp able head.

In various embodiments, the lock includes a sliding catch biased into a locking position.

In various embodiments, the lock includes a rotatable wheel having an internal slot.

In various embodiments, the lock includes a hook pivotably connected to the first handle member. The lock may further include a stop that engages the first handle portion and resists movement of the second handle portion toward the first handle portion. The lock may also include a spring member extending from an end of the lock opposite the hook that engages a slot in the first handle member.

In various embodiments, the first instrument portion and the second instrument portion form one of: a clamp, scissors, forceps, dissector, needle holder, and chest tube passer.

Various embodiments relate to a surgical instrument including: a first handle member having a first handle portion and a first shaft portion; a first end member connected to the first handle member having a first instrument portion and a tab; a second end member connected to the tab of the first end member having a second instrument portion and a shaft portion; a second handle member connected to the shaft portion of the second end member; and lockable means for removably connecting the second handle member to the first handle member.

In various embodiments, the instrument further includes ratchet means for incrementally fixing the position of the second handle member relative to the first handle member.

In various embodiments, the instrument further includes spring means for retaining the lockable means in a closed position.

Various embodiments relate to a surgical instrument including: a first handle member having a first handle portion and a first shaft portion; a first end member having a first instrument portion and a tab pivotably connected to the first handle member; a second end member pivotably connected to the tab of the first end member having a second instrument portion and a shaft portion; a second handle member having a second handle portion and an extension pivotably connected to the shaft portion of the second end member such that movement of the second handle portion toward the first handle portion causes the first instrument portion to rotate toward the second instrument portion; and a lock releasably and pivotably connecting the second handle member to the shaft portion of the first handle member, wherein releasing the lock allows the first handle portion to separate from the second handle portion while the first end member remains connected to the second end member.

Various embodiments further include a first ratchet surface extending from an end of the first handle portion opposite the first shaft portion toward the second handle portion and a second ratchet surface extending from an end of the second handle portion opposite the connection to the second end member toward the first handle portion and facing the opposite direction of the first ratchet surface such that the second ratchet surface incrementally engages the first ratchet surface as the first handle portion and the second handle portion are moved towards each other.

Various embodiments further include a pin at an end of the extension and a slot in the first handle member wherein the lock, in a closed position, retains the pin within the slot.

In various embodiments, when the lock is in a closed position, the first shaft portion is parallel to the second shaft portion and when the lock is released, the first shaft portion is free to rotate relative to the second shaft portion.

The foregoing objects and advantages of the invention are illustrative of those that can be achieved by the various exemplary embodiments and are not intended to be exhaustive or limiting of the possible advantages that can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

BRIEF DESCRIPTION OF THE DRAWINGS

In order to better understand various exemplary embodiments, reference is made to the accompanying drawings, wherein:

FIG. 6A shows a another exemplary locking mechanism having a sliding catch;

FIG. 6B shows a side plan view of an exemplary sliding catch;

FIG. 6C shows a top plan view of an exemplary sliding catch;

DETAILED DESCRIPTION

Figure 1:
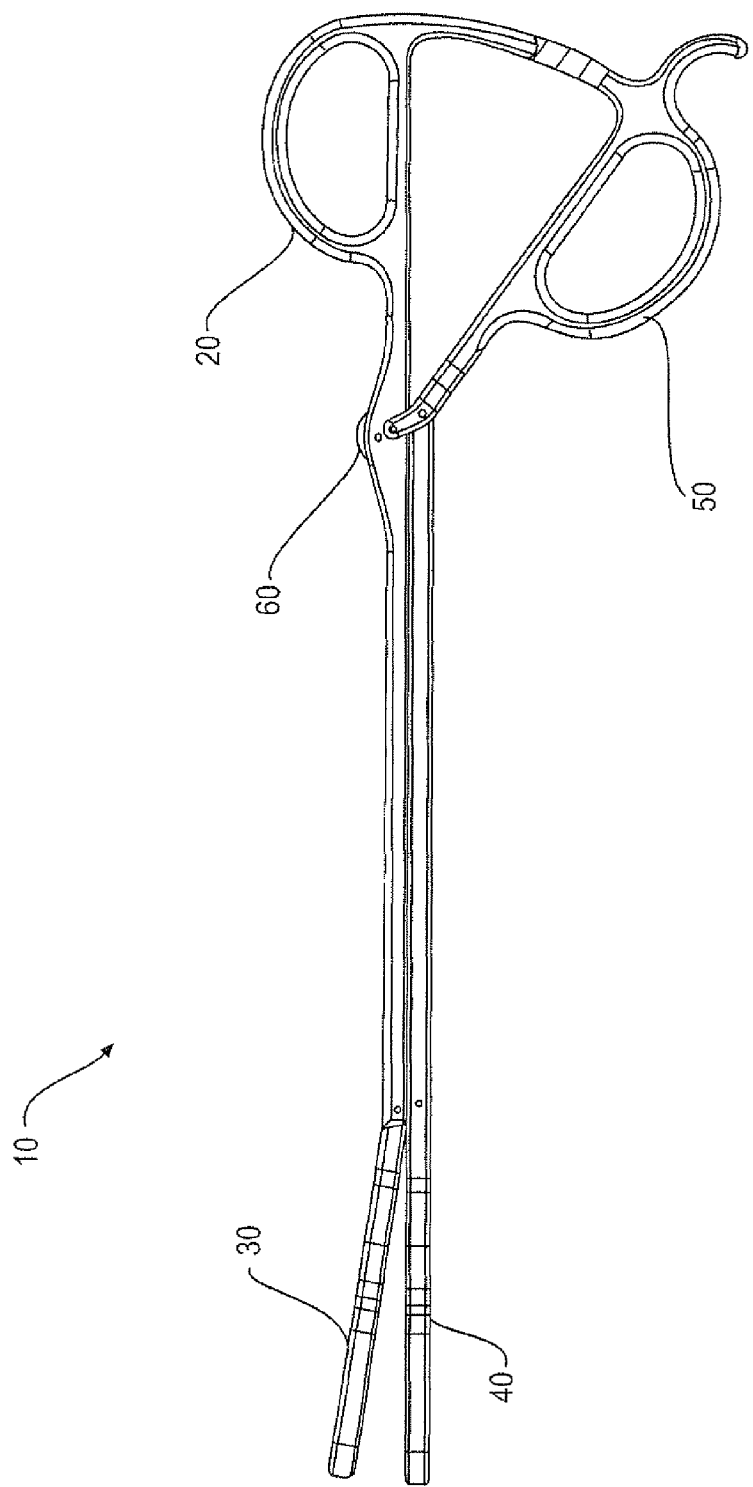
FIG. 1 shows a side plan view of an exemplary surgical instrument.

Referring now to the drawings, in which like numerals refer to like components or steps, there are disclosed various exemplary embodiments.

Figure 2:
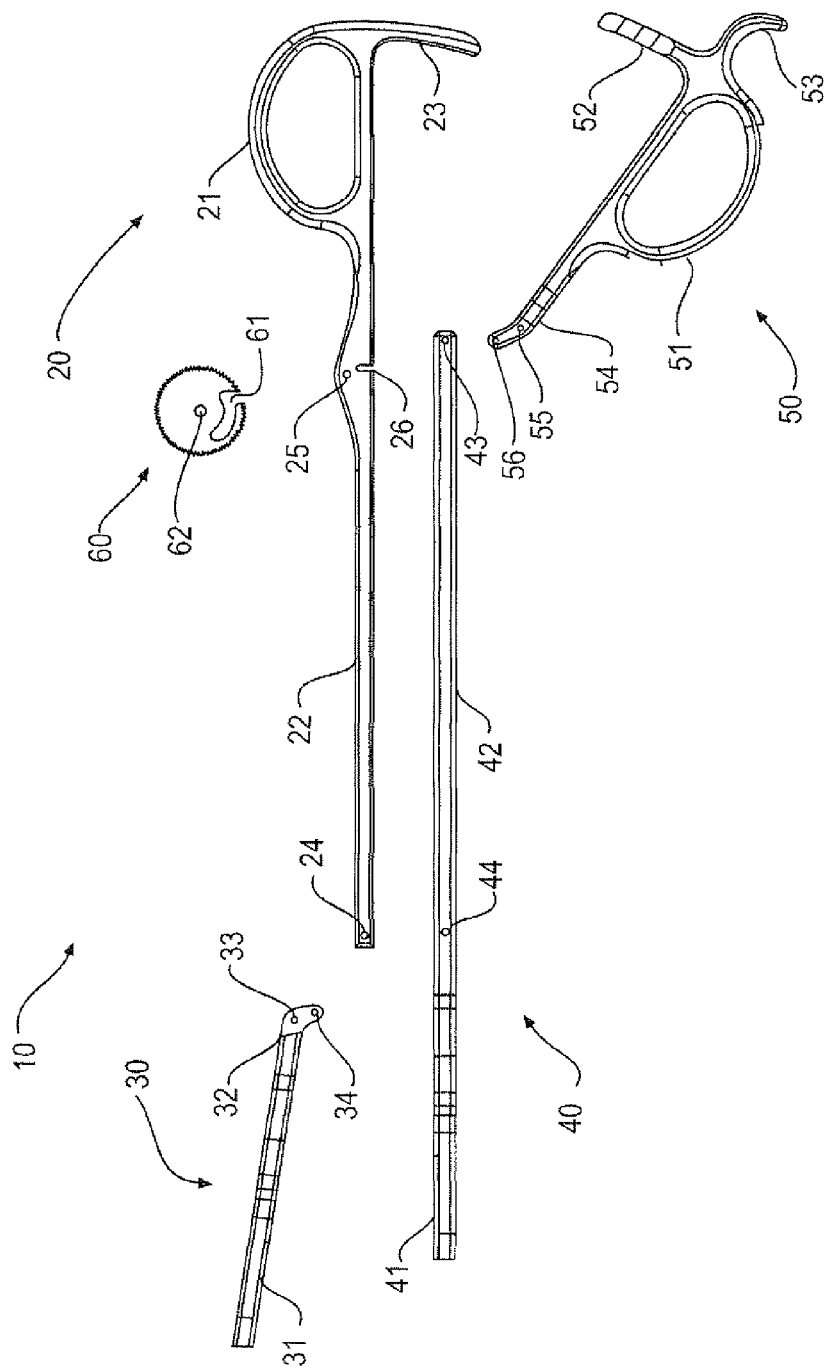
FIG. 2 shows an exploded view of the instrument in FIG. 1.
Figure 3:
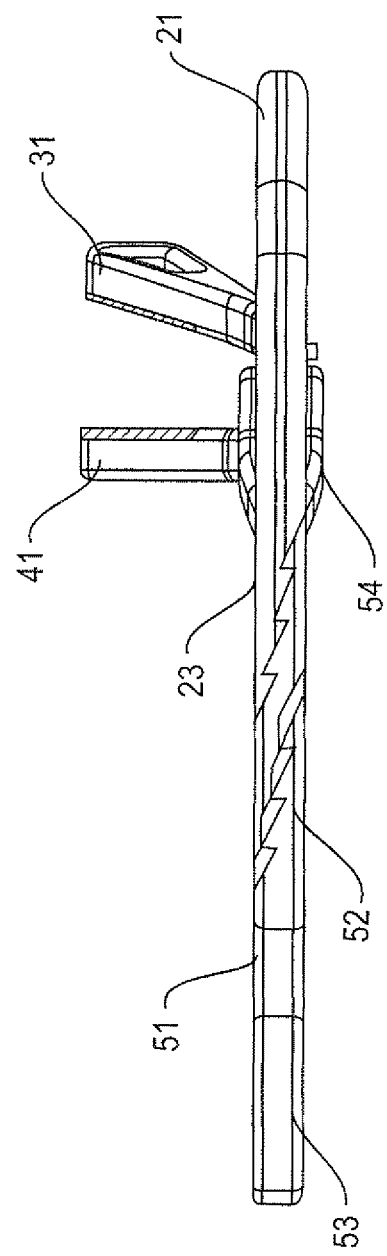
FIG. 3 shows a rear plan view of the instrument in FIG. 1.

FIGS. 1-3 show a surgical instrument 10. The instrument 10 includes a first handle member 20, a first end member 30, a second end member 40, a second handle member 50, and a lock 60. The first handle member 20 and the second handle member 50 are located at a proximal end of instrument 10. The first end member 30 and the second end member 40 are located at a distal end of instrument 10.

The first handle member 20 is provided with a handle portion 21. The handle portion 21 forms an oblong loop. The first handle member 20 is further provided with a shaft portion 22 that extends from one end of handle portion 21. A first ratchet surface 23 extends from the other end of handle portion 21. The first ratchet surface 23 includes a plurality of stepped angular teeth. Various alternative embodiments may exclude the first ratchet surface 23. For example, a scissors instrument may not include a first rachet surface. The shaft portion 22 is provided with a pivot point 24 at the end of the shaft opposite handle portion 21. The shaft portion 22 is further provided with a pivot point 25 located between the handle portion 21 and the pivot point 24. The shaft portion 26 is further provided with a slot 26 located between the handle portion 21 and the pivot point 24 near the pivot point 26.

The first end member 30 is provided with a first instrument portion 31. The end of the first instrument portion 31 forms a loop. The inner surface of first instrument portion 31 includes a ridged, checked, or roughened surface. The first end member 30 is further provided with a tab 32 located at the proximal end of the first end member 30. The tab 32 is L-shaped, extending inwardly. The tab 32 includes a first pivot point 32 and a second pivot point 34. The pivot point 33 is connected to pivot point 24 forming a pivotable connection.

The second end member 40 is provided with a second instrument portion 41. The end of the second instrument portion 41 forms a loop. The inner surface of the second instrument portion 41 includes a ridged, checked, or roughened surface. The second end member 40 is further provided with a shaft portion 42 extending proximally from the second end portion 41. A pivot point 43 is located at a proximal end of shaft portion 42. A pivot point 44 is located between second instrument portion 41 and shaft portion 42. The pivot point 44 is connected to pivot point 34 forming a pivotable connection.

The second handle member 50 is provided with a second handle portion 51. The second handle portion 51 forms an oblong loop. The second handle member 50 is further provided with a second ratchet surface 52 extending inwardly from a proximal end of handle portion 51. The second ratchet surface 52 includes a plurality of stepped angular teeth. The teeth of second ratchet surface 52 face the opposite direction from the teeth of first ratchet surface 23. In various alternative embodiments excluding the first ratchet surface 23, the second ratchet surface 52 may also be excluded. The second handle member 50 is further provided with a finger grip 53 extending proximally from the proximal end of second handle portion 51. The finger grip 53 curves outwardly as it extends away from second handle portion 51. The second handle member 50 is further provided with an extension 54 extending distally from the distal end of handle portion 51. The extension 54 includes a first pivot point 55 and a second pivot point 56. The pivot point 55 is connected to pivot point 43 forming a pivotable connection. The pivot point 56 is releasably connectable to pivot point 35 and/or slot 26 forming a releasable pivotable connection.

The lock 60 is circular shaped. The outer surface of lock 60 is includes slots, teeth, or a roughened surface. The lock 60 is provided with a slot 61. The slot 61 is L-shaped with an opening in the circumference of lock 60. The slot 61 extends in an arc parallel to a portion of the circumference of lock 60. The lock 60 is further provided with a through hole 62. The through hole 62 may be connected to the pivot point 25 by a pin, allowing the lock 60 to rotate about the through hole 62.

Having described the various components of the exemplary surgical instrument 10, a description of the operation of the instrument 10 will be provided. The instrument 10 may be used in a closed configuration. The lock 60 may retain pivot point 56 forming a pivotable connection. The first handle member 20 and the second handle member 50 may be manually grasped like scissors. The finger grip 53 may provide additional control and leverage. As the first handle member 20 is brought toward the second handle member 50, the teeth of the ratchet surfaces 23 and 53 may incrementally engage each other. Because the ratchet surfaces 23 and 53 are located at the end of handle portions 21 and 51, the engaged ratchet surfaces 23 and 53 may provide an additional convenient handle for grasping and rotating instrument 10. The engaged ratchet surfaces 23 and 53 may be released by applying pressure to each of the handle portions 21 and 51 in the direction opposite the ratchet surfaces such that the teeth separate. In various alternative embodiments without the ratchet surfaces 23 and 53, the handle members 20 and 50 may move freely without engaging each other.

Moving the first handle member 20 and the second handle member 50 together causes the first instrument portion 31 to rotate toward the second instrument portion 41, closing the instrument 10. In particular, as the first handle portion 21 and the second handle portion 21 are brought together, the second handle member 50 rotates about the pivot point 56. The pivot point 55 moves proximally relative to the pivot point 56, moving the second shaft portion 40 proximally relative to the first shaft portion 22. The pivot point 44 moves the pivot point 34 proximally relative to pivot point 33, causing first end member 30 to rotate about the pivot point 33. As the first end member 30 rotates, the first instrument portion 31 is brought closer to the second instrument portion 41, closing the instrument 10.

The surgical instrument 10 includes a narrow central portion formed by the first shaft portion 22 and the second shaft portion 42. During use, the shaft portions move parallel to each other, maintaining the narrow structure. The instrument 10 can therefore be used in various surgical settings, including minimally invasive surgery, requiring access through a narrow passage such as a small incision or a port such as a trocar.

Figure 4:
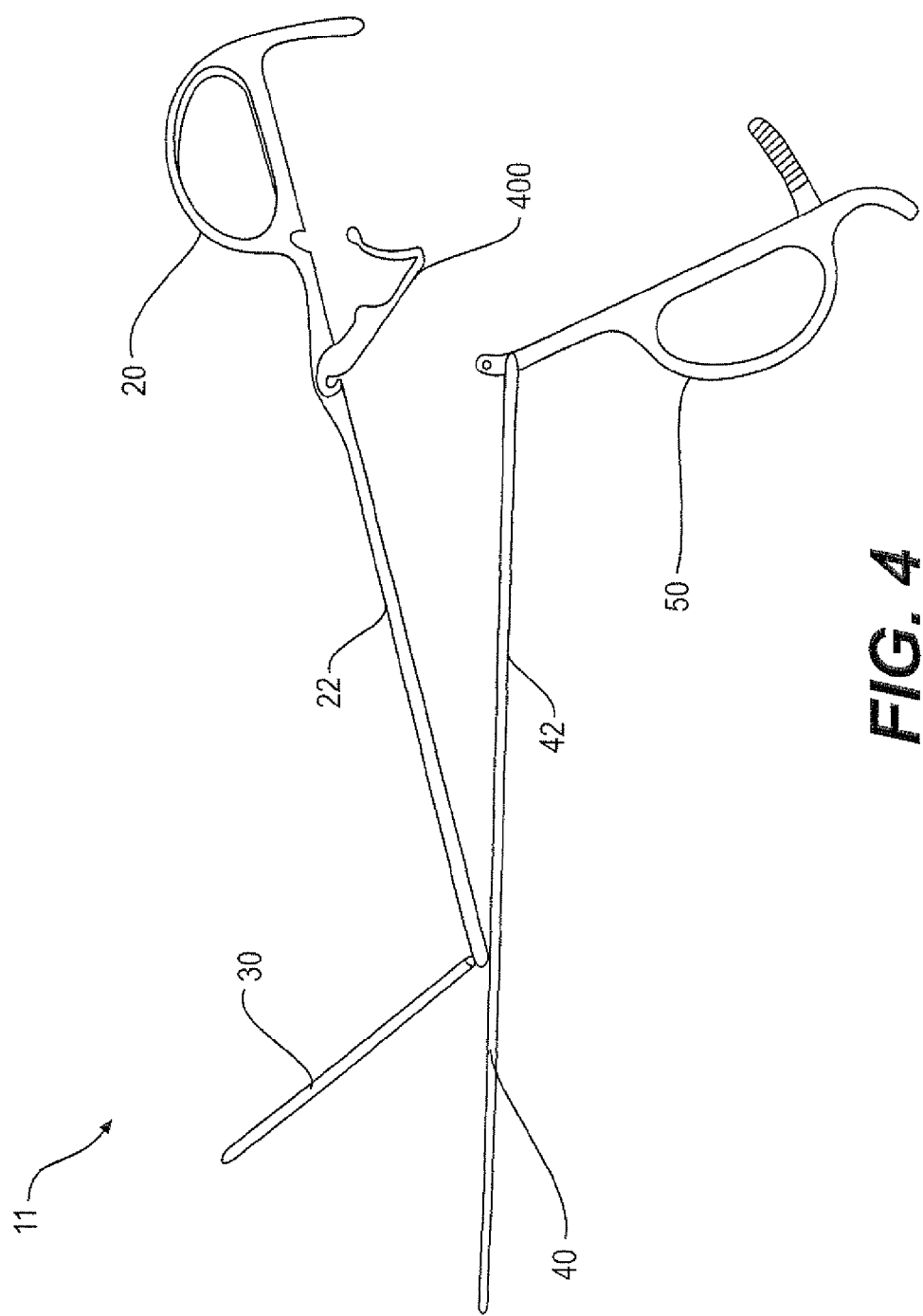
FIG. 4 shows a plan view of another exemplary surgical instrument in an open configuration.

FIG. 4 shows a side plan view of another exemplary surgical instrument 10 in an open configuration. In the open configuration, the lock 400 is in a released position, which allows a pivot point 56 of the second handle member 50 to be removed from the slot 26. The first handle member 20 remains connected to the first end member 30, the first end member 30 remains connected to the second end member 40, and the second end member 40 remains connected to the second handle member 50. Accordingly, the components of instrument 10 remain connected, so there are no loose parts. Further, the first shaft portion 22 can rotate relative to the second shaft portion 42, exposing the inner surfaces of the shaft portions for cleaning.

Figure 5A:
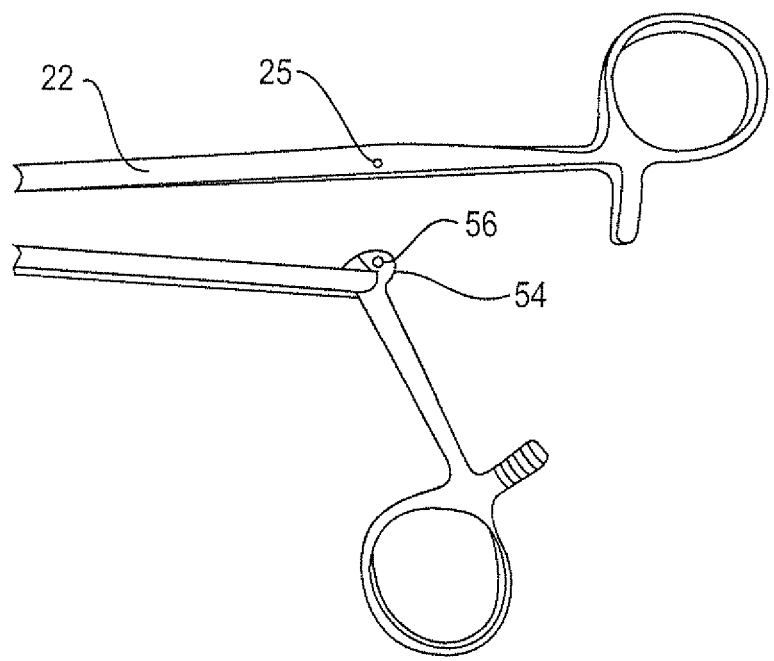
FIG. 5A shows an exemplary locking mechanism in an open configuration.
Figure 5B:
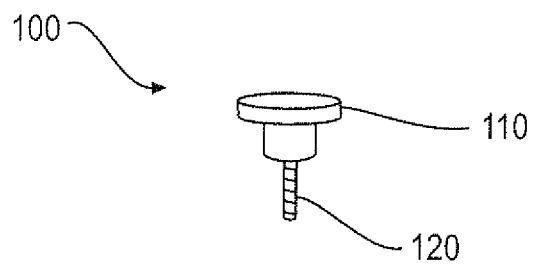
FIG. 5B shows another component of the exemplary locking mechanism shown in FIG. 5A.

FIGS. 5A and 5B show an exemplary locking mechanism 100 for use with instrument 10. As shown in FIG. 5A, the instrument 10 includes a through hole 25. The pivot point 55 is also a through hole. As shown in FIG. 5B, the locking mechanism 100 includes a head 110 and a threaded shaft 120. The through hole 25 and the pivot point 55 are internally threaded to accept the threaded shaft 120. The head 110 may be manually gripped and rotated. The threaded shaft 120 may be screwed into the through hole 25 and the pivot point 55 forming a releasable pivotable connection. The threaded shaft 120 allows the second handle member 50 to rotate about the pivot point 55.

FIGS. 6A, 6B, and 6C show another exemplary locking mechanism 200 for use with the instrument 10. As shown in FIG. 6A, the instrument 10 includes a slot 26. The pivot point 56 is a pin extending through the extension 54. The pin fits within the slot 26 and is held in place by the locking mechanism 200. The locking mechanism 200 is a sliding catch. The locking mechanism 200 is provided with a forked retainer 210. The forked retainer 210 includes two prongs that engage each side of the extension 54 and the pivot point 56. The locking mechanism 200 is further provided with a body 220 including a groove 230. The body 220 may be manually grasped and slid proximally to release the pin from the forked retainer 210. The locking mechanism 200 is further provided with a vertical pin 240. The vertical pin 240 resides within a slot in the first shaft portion 22 and includes a head for retaining locking mechanism 200 in sliding relation to the first shaft portion 22. The locking mechanism 200 is further provided with a spring 250 that resides within the slot of the first shaft portion 22. The spring 250 biases the locking mechanism 200 distally such that the forked retainer 210 is biased toward a locking position. The locking mechanism 200 is further provided with a groove 260 within the body 220. The groove 260 holds the first shaft portion 22 and further retains the locking mechanism 200.

Figure 7:
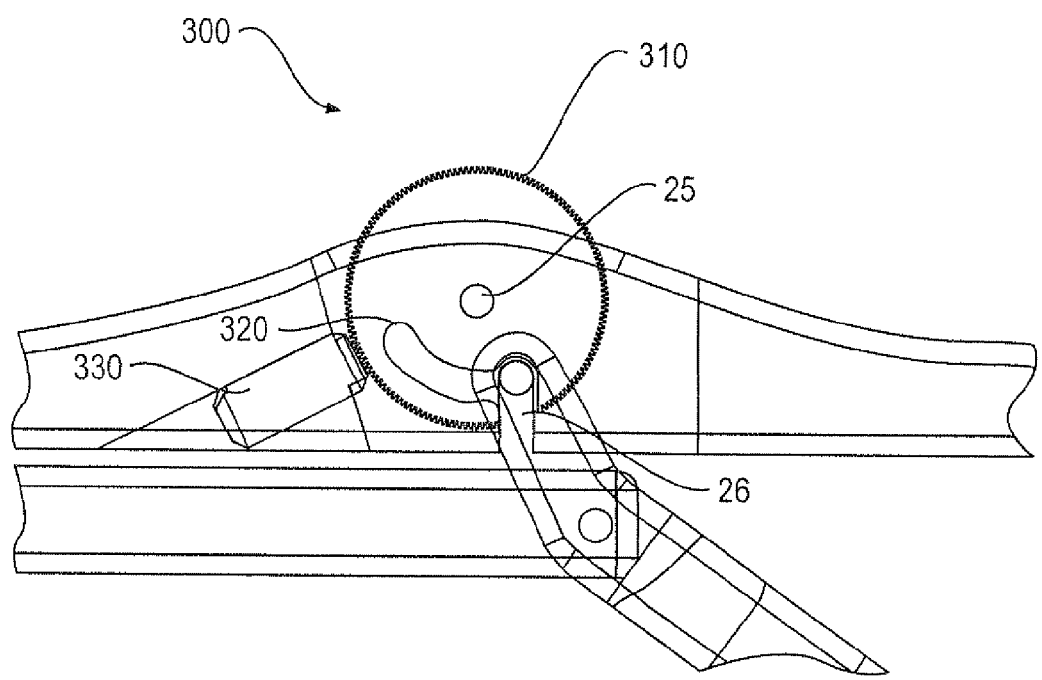
FIG. 7 shows another exemplary locking mechanism.

FIG. 7 shows another exemplary locking mechanism 300 for use with the instrument 10. The extension 54 has a forked end with the pivot point 56 being a pin extending between the two prongs. The locking mechanism 300 is provided with a wheel 310. The wheel 310 is located within a slot in the first shaft portion 22. The wheel 310 includes a through hole that aligns with through hole 25 and is held by a pin, allowing the wheel 310 to rotate about the through hole 25. The wheel 310 includes an L-shaped slot 320. The L-shaped slot 320 has an opening in the circumference of the wheel 310 and extends in an arc parallel to a portion of the circumference of the wheel 310. The opening of the L-shaped slot 320 may be aligned with the slot 26 to allow a pin 56 to be inserted vertically into slot 26. The wheel 310 may be rotated such that the pin 56 moves within the arc portion of slot 320 until the opening is no longer aligned with the slot 26, thereby retaining the pin 56 within the slot 26. The locking mechanism 300 is further provided with a friction device 330 that frictionally engages the circumference of wheel 310.

Figure 8A:
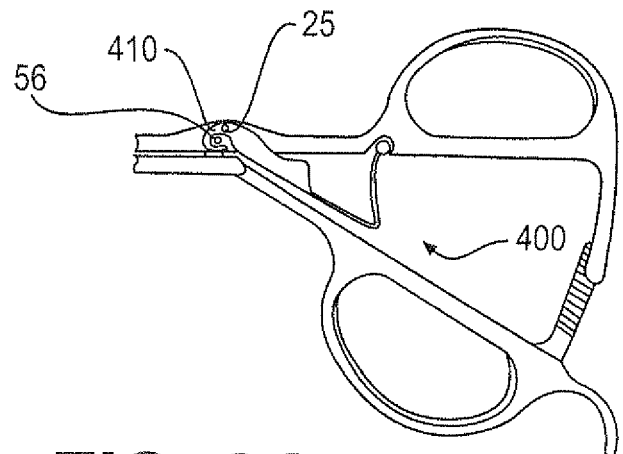
FIG. 8A shows another exemplary locking mechanism in a closed configuration.
Figure 8B:
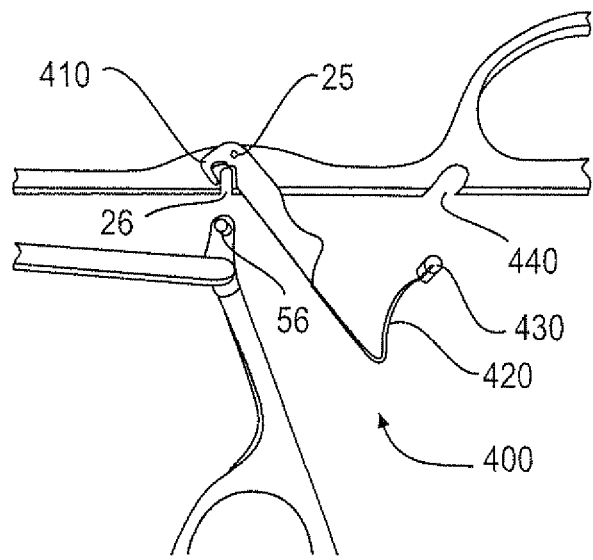
FIG. 8B shows the exemplary locking mechanism of FIG. 8A in an open configuration.

FIGS. 8A and 8B show another exemplary locking mechanism 400. The locking mechanism 400 is provided with a hook portion 410. The locking mechanism 400 is pivotably connected to the shaft portion 22 at a through hole 25. In a closed position shown in FIG. 8A, the hook portion 410 extends across the slot 26, retaining the pivot point 56 within the slot 26. In an open position, shown in FIG. 8B, the opening of hook portion 410 aligns with the slot 26 allowing the pivot point 56 to be removed from the slot 26. The locking mechanism 400 is further provided with a curved spring portion 420. The curved spring portion 420 extends at an acute angle from an end of the hook portion 410. The end of the curved spring portion 420 includes a cylinder 430 that engages a slot 440 located in the first handle portion 21. The curved spring portion 420 biases locking mechanism 400 into the closed position. In the closed position, the curved spring portion 420 extends between the first handle portion 21 and the second handle portion 51. As the handle portions of instrument 10 are squeezed together, curved spring portion 420 provides resistance.

The above described embodiments include a plurality of pivot points and pivotable connections. A pivot point may be any structure allowing a piece to pivot about an axis. For example, pivot points may include through holes, indents, the closed ends of slots, pins, studs, and shafts. A pivotable connection may be made by connecting two pieces at two pivot points in any manner that allows at least one of the pieces to pivot. For example, in the exemplary embodiment shown in FIGS. 1-3, a pivotable connection is made between the pivot point 43 and the pivot point 55. As best seen in FIG. 3, the extension 54 is a fork. The pivot point 55 may be formed as a pin extending through the pivot point 55 and the pivot point 43. As another example, the pivot point 24 and the pivot point 44 may include a slot cut in shaft portion 22, and shaft portion 42, respectively. The pivot point 33 and the pivot point 34 may be through holes extending through tab 32. The pivotable connections may be made by placing tab 32 within the slot and connecting the pivot point 33 to the pivot point 24 with a pin and connecting the pivot point 34 to the pivot point 44 with a pin. As yet another example, as shown in FIG. 5A, the shaft portion 22 and the extension 54 may be solid pieces that align next to each other. The pivot point 24 and the pivot point 56 may be through holes. A pivotable connection may be made by placing a pin, such as the threaded shaft 120 through the pivot point 24 and the pivot point 56. It should be apparent that various types of pivotable connections may be used in combination to connect the plurality of pivot points.

The above described exemplary embodiments show first instrument member 30 and second instrument member 40 forming a forceps. As best seen in FIG. 3, the forceps may be curved to one side and have a closed loop shape. Other instruments having instrument members that rotate together about a pivotable connection may also be formed using the principles described above. Other exemplary instruments include but are not limited to, scissors, clamps, other varieties of forceps, dissectors, needle holders, and chest tube passers.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A surgical instrument, comprising:
   a first handle member having a first handle portion and a first shaft portion;
   a first end member having a first instrument portion and a tab, said tab releasably connected to the first shaft portion;
   a second end member connected to the tab of the first end member having a second instrument portion and a shaft portion;
   a second handle member connected to the shaft portion of the second end member; and
   a lock that releasably connects the second handle member to the shaft portion of the first handle member,
   wherein when the first handle member is released from the second handle member, the first handle member is rotatable towards the first end member, and the second handle member is detachably connected to the shaft portion of the second end member.

2. The surgical instrument of claim 1, wherein the first handle portion has a first ratchet surface extending from an end of the first handle portion and the second handle portion has a second ratchet surface extending from an end of the second handle portion.

3. The surgical instrument of claim 1, wherein the shaft portion of the first handle member defines a slot, and the lock is configured to releasably retains a pin within the slot.

4. The surgical instrument of claim 1, wherein the lock comprises a threaded shaft having graspable head.

5. The surgical instrument of claim 1, wherein the lock comprises a sliding catch biased into a locking position.

6. The surgical instrument of claim 1, wherein the lock comprises a rotatable wheel having an internal slot.

7. The surgical instrument of claim 1, wherein the lock comprises a hook pivotably connected to the first handle member.

8. The surgical instrument of claim 7, wherein the lock further comprises a stop that engages the first handle portion and resists movement of the second handle portion toward the first handle portion.

9. The surgical instrument of claim 7, wherein the lock further comprises a spring member extending from an end of the lock opposite the hook that includes a cylinder that engages a slot in the first handle member.

10. The surgical instrument of claim 1, wherein the first instrument portion and the second instrument portion form a clamp.

11. The surgical instrument of claim 1, wherein the first instrument portion and the second instrument portion form a scissors.

12. The surgical instrument of claim 1, wherein the first instrument portion and the second instrument portion form a forceps.

13. A surgical instrument, comprising:
   a first handle member having a first handle portion and a first shaft portion;
   a first end member having a first instrument portion and a tab, said tab releasably connected to the first shaft portion;
   a second end member connected to the tab of the first end member having a second instrument portion and a shaft portion;
   a second handle member connected to the shaft portion of the second end member; and
   lockable means for removably connecting the second handle member to the first handle member,
   wherein when the first handle member is released from the second handle member, the first handle member is rotatable towards the first end member, and the second handle member is detachably connected to the shaft portion of the second end member.

14. The surgical instrument of claim 13, further comprising ratchet means for incrementally fixing the position of the second handle member relative to the first handle member.

15. The surgical instrument of claim 13, further comprising spring means for biasing the lockable means in a closed position.

16. The surgical instrument of claim 13, wherein the first instrument portion and the second instrument portion form one of: a clamp, scissors, forceps, dissector, needle holder, and chest tube passer.

17. A surgical instrument, comprising:
   a first handle member having a first handle portion and a first shaft portion;
   a first end member having a first instrument portion and a tab pivotably connected to the first handle member;
   a second end member pivotably connected to the tab of the first end member having a second instrument portion and a shaft portion;
   a second handle member having a second handle portion and an extension pivotably connected to the shaft portion of the second end member such that movement of the second handle portion toward the first handle portion causes the first instrument portion to rotate toward the second instrument portion; and
   a lock that releasably and pivotably connects the second handle member to the shaft portion of the first handle member, wherein releasing the lock allows the first handle portion to separate from the second handle portion while the first end member remains connected to the second end member and the second handle portion is detachably connected to the shaft portion of the second end member.

18. The instrument of claim 17, further comprising a first ratchet surface extending from an end of the first handle portion opposite the first shaft portion toward the second handle portion and a second ratchet surface extending from an end of the second handle portion opposite the connection to the second end member toward the first handle portion and facing the opposite direction of the first ratchet surface such that the second ratchet surface incrementally engages the first ratchet surface as the first handle portion and the second handle portion are moved towards each other.

19. The instrument of claim 17, further comprising a pin at an end of the extension and a slot in the first handle member wherein the lock, in a closed position, retains the pin within the slot.

20. The instrument of claim 17, wherein when the lock is in a closed position, the first shaft portion is parallel to the second shaft portion and when the lock is released, the first shaft portion is free to rotate relative to the second shaft portion.

* * * * *